(12) United States Patent
Patterson et al.

(10) Patent No.: US 6,303,293 B1
(45) Date of Patent: Oct. 16, 2001

(54) OLIGONUCLEOTIDE REVERSE TRANSCRIPTION PRIMERS FOR EFFICIENT DETECTION OF HIV-1 AND HIV-2 AND METHODS OF USE THEREOF

(75) Inventors: David R. Patterson, San Diego, CA (US); John A. Puskas, Rochester, NY (US); Keming Song, Ballwin, MO (US); Jeffrey M. Linnen, San Diego, CA (US)

(73) Assignee: Ortho-Clinical Diagnostics, Inc., Raritan, NJ (US)

( * ) Notice: Subject to any disclaimer, the term of this patent is extended or adjusted under 35 U.S.C. 154(b) by 0 days.

(21) Appl. No.: 09/494,102

(22) Filed: Jan. 28, 2000

Related U.S. Application Data

(60) Provisional application No. 60/118,417, filed on Feb. 2, 1999.

(51) Int. Cl.[7] .................................................... C12Q 1/70
(52) U.S. Cl. ................. 435/5; 435/6; 536/23.1; 536/24.3; 536/24.31; 536/24.32; 536/24.33
(58) Field of Search .................... 435/5, 6; 536/23.1, 536/24.3, 24.31, 24.32, 24.33

(56) References Cited

U.S. PATENT DOCUMENTS

| | | | |
|---|---|---|---|
| 5,478,724 | 12/1995 | Morse et al. .................... | 435/5 |
| 5,688,637 | 11/1997 | Moncany et al. ................ | 435/6 |
| 5,840,480 | 11/1998 | Guertler et al. ................. | 435/5 |
| 6,001,558 | * 12/1999 | Backus et al. ................... | 435/5 |

FOREIGN PATENT DOCUMENTS

| | | | |
|---|---|---|---|
| 0 887 427A2 | 12/1998 | (EP) ................. | C12Q/1/70 |
| 98/58086 | 12/1998 | (WO) ................ | C12Q/1/70 |

* cited by examiner

*Primary Examiner*—Jeffrey Stucker
(74) *Attorney, Agent, or Firm*—Darby & Darby

(57) ABSTRACT

Disclosed herein are methods and kits for the detection of human immunodeficiency virus in biological samples from human subjects. Oligonucleotide reverse transcription primers for use in such methods and kits for detection of human immunodeficiency virus are also described.

18 Claims, 2 Drawing Sheets

SEQUENCE LISTING

```
<160> NUMBER OF SEQ ID NOS:   13

<210> SEQ ID NO 1
<211> LENGTH: 15
<212> TYPE: DNA
<213> ORGANISM: Artificial sequence
<220> FEATURE:
<221> NAME/KEY: misc_feature
<223> OTHER INFORMATION: Oligonucleotide primer

<400> SEQUENCE: 1
cttgtattac tactg                                                        15

<210> SEQ ID NO 2
<211> LENGTH: 12
<212> TYPE: DNA
<213> ORGANISM: Artificial sequence
<220> FEATURE:
<221> NAME/KEY: misc_feature
<223> OTHER INFORMATION: Oligonucleotide primer

<400> SEQUENCE: 2
ccctgtggcg cc                                                           12

<210> SEQ ID NO 3
<211> LENGTH: 15
<212> TYPE: DNA
<213> ORGANISM: Artificial sequence
<220> FEATURE:
<221> NAME/KEY: misc_feature
<223> OTHER INFORMATION: Oligonucleotide primer
```

<400> SEQUENCE: 3
gcgactagga gaaga                                                         15

<210> SEQ ID NO 4
<211> LENGTH: 14
<212> TYPE: DNA
<213> ORGANISM: Artificial sequence
<220> FEATURE:
<221> NAME/KEY: misc_feature
<223> OTHER INFORMATION: Oligonucleotide primer

<400> SEQUENCE: 4
cccagacgct cagt                                                          14

<210> SEQ ID NO 5
<211> LENGTH: 150
<212> TYPE: DNA
<213> ORGANISM: Artificial sequence
<220> FEATURE:
<221> NAME/KEY: misc_feature
<223> OTHER INFORMATION: target nucleic acid for an internal positive
      control

<400> SEQUENCE: 5
cgccagcgtg gaccatcaag tagtaatgaa cgcacggacg aggacatcat agagattaca        60
cctttatcca cagttctcgg tctaacgcag cagtcagtgt atcagcacca gcatccgtag       120
tgatctttca gtgtctgctc caggatcgtg                                        150

<210> SEQ ID NO 6
<211> LENGTH: 30
<212> TYPE: DNA
<213> ORGANISM: Artificial sequence
<220> FEATURE:
<221> NAME/KEY: misc_feature
<223> OTHER INFORMATION: Oligonucleotide primer

<400> SEQUENCE: 6
ctgcttaagc tcaataaag cttgccttga                                          30

<210> SEQ ID NO 7
<211> LENGTH: 29
<212> TYPE: DNA
<213> ORGANISM: Artificial sequence
<220> FEATURE:
<221> NAME/KEY: misc_feature
<223> OTHER INFORMATION: Oligonucleotide primer

<400> SEQUENCE: 7
gggtctgagg gatctctagt taccagagt                                          29

<210> SEQ ID NO 8
<211> LENGTH: 23
<212> TYPE: DNA
<213> ORGANISM: Artificial sequence
<220> FEATURE:
<221> NAME/KEY: misc_feature
<223> OTHER INFORMATION: Oligonucleotide primer

<400> SEQUENCE: 8
tgttcgggcg ccactgctag aga                                                23

<210> SEQ ID NO 9
<211> LENGTH: 24
<212> TYPE: DNA
<213> ORGANISM: Artificial sequence

```
<220> FEATURE:
<221> NAME/KEY: misc_feature
<223> OTHER INFORMATION: Oligonucleotide primer

<400> SEQUENCE: 9
gggaggttct ctccagcact agca                                            24

<210> SEQ ID NO 10
<211> LENGTH: 26
<212> TYPE: DNA
<213> ORGANISM: Artificial sequence
<220> FEATURE:
<221> NAME/KEY: misc_feature
<223> OTHER INFORMATION: Oligonucleotide primer

<400> SEQUENCE: 10
gcgactagga gagatgggaa cacaca                                          26

<210> SEQ ID NO 11
<211> LENGTH: 22
<212> TYPE: DNA
<213> ORGANISM: Artificial sequence
<220> FEATURE:
<221> NAME/KEY: misc_feature
<223> OTHER INFORMATION: Oligonucleotide primer

<400> SEQUENCE: 11
caacagacgg gcacacacta ct                                              22

<210> SEQ ID NO 12
<211> LENGTH: 22
<212> TYPE: DNA
<213> ORGANISM: Artificial sequence
<220> FEATURE:
<221> NAME/KEY: misc_feature
<223> OTHER INFORMATION: Oligonucleotide primer

<400> SEQUENCE: 12
gaacagatgg gcacacactg ct                                              22

<210> SEQ ID NO 13
<211> LENGTH: 25
<212> TYPE: DNA
<213> ORGANISM: Artificial sequence
<220> FEATURE:
<221> NAME/KEY: misc_feature
<223> OTHER INFORMATION: Oligoncucleotide primer

<400> SEQUENCE: 13
ccacgcttgc ttgcttaaag acctc                                           25
```

OLIGONUCLEOTIDE REVERSE TRANSCRIPTION PRIMERS FOR EFFICIENT DETECTION OF HIV-1 AND HIV-2 AND METHODS OF USE THEREOF

This application claims priority under 35 U.S.C. § 119(e) to U.S. provisional application Ser. No. 60/118,417 filed on Feb. 2, 1999.

FIELD OF THE INVENTION

The present invention pertains to improved methods for detecting nucleic acid sequences in biological samples, particularly sequences derived from infectious microorganisms.

BACKGROUND OF THE INVENTION

Millions of individuals world-wide are infected with Human Immunodeficiency Virus (HIV). Consequently, HIV infection represents a serious public health concern. Spread of HIV infection via contaminated blood products means that there is a need for screening methods that can detect small amounts of HIV RNA in patient samples. Furthermore, the increasing availability of ameliorative treatments for HIV infection means that early detection of infection in a patient is vital in order to initiate appropriate therapeutic interventions.

Thus, there is a need in the art for highly sensitive detection methods for HIV that can be used in diagnosis and screening.

SUMMARY OF THE INVENTION

The present invention provides a method for reverse transcribing Human Immunodeficiency Virus (HIV) RNA in a biological sample, where the method comprises:
  (a) contacting RNA derived from said sample with an oligonucleotide under conditions in which said oligonucleotide primes synthesis of DNA complementary to at least a portion of said RNA;
  wherein said oligonucleotide is selected from the group consisting of
    (i) 5'-CTTGTATTACTACTG-3'<SEQ ID NO 1>,
    (ii) 5'-CCCTGTGGCGCC-3'<SEQ ID NO 2>,
    (iii) 5'-GCGACTAGGAGAGA-3'<SEQ ID NO 3>,
    (iv) 5'-CCCAGACGGTCAGT-3'<SEQ ID NO 4>, or
    (v) any combination of any of the foregoing.

In another aspect, the invention provides a method for detecting the presence of Human Immunodeficiency Virus (HIV) RNA in a biological sample, where the method comprises:
  (a) performing a reverse transcription reaction using as a template RNA derived from the sample and using, as a primer, an oligonucleotide complementary to a nucleotide sequence contained within the RNA to produce HIV-specific reverse transcription products,
  where the primer is selected from the group consisting of:
    (i) 5'-CTTGTATTACTACTG-3'<SEQ ID NO 1>,
    (ii) 5'-CCCTGTGGCGCC-3'<SEQ ID NO 2>,
    (iii) 5'-GCGACTAGGAGAGA-3'<SEQ ID NO 3>,
    (iv) 5'-CCCAGACGGTCAGT-3'<SEQ ID NO 4>, or
    (v) any combination of any of the foregoing;
  (b) amplifying products of the reverse transcription reaction to produce amplification products; and
  (c) detecting the amplification products;
  where detection of the amplification products indicates the presence of HIV RNA in the sample.

Amplification may be carried out by any method, preferably polymerase chain reaction (PCR). The use of HIV-specific reverse transcription primers according to the invention provides a sensitive method for detecting HIV-1 and/or HIV-2 in a sample, preferably plasma.

In yet another aspect, the invention provides kits for the detection of HIV-1, HIV-2, or a combination thereof in a biological sample, where the kit comprises a reverse transcription primer selected from the group consisting of:
  (a) 5'-CTTGTATTACTACTG-3'<SEQ ID NO 1>,
  (b) 5'-CCCTGTGGCGCC-3'<SEQ ID NO 2>,
  (c) 5'-GCGACTAGGAGAGA3'<SEQ ID NO 3>,
  (d) 5'-CCCAGACGGTCAGT-3'<SEQ ID NO 4>, or
  (e) any combination of any of the foregoing. The kits may additionally comprise reagents and instructions for reverse transcription, amplification, and product detection.

DETAILED DESCRIPTION OF THE INVENTION

Figure 1:
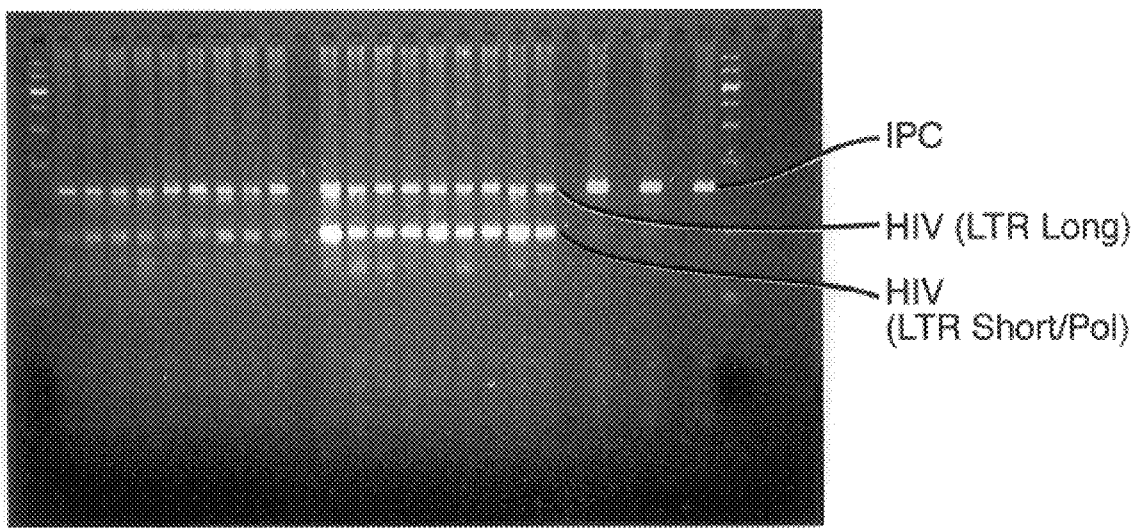
FIG. 1 is a photographic illustration of a 4% agarose gel stained with ethidium bromide showing HIV-1-specific amplification products obtained using as a reverse transcription primer (a) random hexamer primers (lanes 2–10); or (b) a mixture of random hexamer primers and LTR8RT (lanes 12–20). Lane 1 contains markers, and lanes 22, 24, and 26 are control samples.

The present inventors have discovered that detection of Human Immunodeficiency Virus (HIV) RNA in biological samples is more efficient when oligonucleotides having sequences complementary to certain sequences present in HIV RNA are used as primers for reverse transcription. Preferably, the sequences of the primers correspond to sequences near the 3' end of HIV RNA.

Many techniques in molecular biology, microbiology, recombinant DNA, and protein biochemistry are used in practicing the present invention, such as those explained in, for example, *Current Protocols in Molecular Biology*, Volumes I, II, and III, 1997 (F. M. Ausubel ed.); Sambrook el al., 1989, *Molecular Cloning: A Laboratory Manual*, Second Edition, Cold Spring Harbor Laboratory Press, Cold Spring Harbor, N.Y.; *DNA Cloning: A Practical Approach*, Volumes I and II, 1985 (D. N. Glover ed.); *Oligonucleotide Synthesis*, 1984, (M. L. Gait ed.); *Transcription and*

*Translation*, 1984 (Hames and Higgins eds.); *A Practical Guide to Molecular Cloning*; the series, *Methods in Enzymology* (Academic Press, Inc.); and *Protein Purification: Principles and Practice*, Second Edition (Springer-Verlag, N.Y.).

"Nucleic acid" or "polynucleotide" as used herein refers to purine- and pyrimidine-containing polymers of any length, either polyribonucleotides or polydeoxyribonucleotides or mixed polyribo-polydeoxyribo nucleotides. This includes single- and double-stranded molecules, such as, for example, DNA-DNA, DNA-RNA and RNA-RNA hybrids, as well as "protein nucleic acids" (PNA) formed by conjugating bases to an amino acid backbone. This also includes nucleic acids containing modified bases.

A "complement" of a nucleic acid sequence as used herein refers to the antisense sequence that participates in Watson-Crick base-pairing with the original sequence.

A "primer" as used herein is an oligonucleotide between about 5 and about 50 nucleotides in length, preferably between about 6 and about 25 nucleotides in length and most preferably between about 6 and about 18 nucleotides in length, that forms a duplex with a single-stranded nucleic acid sequence of interest and allows polymerization of a complementary strand using, e.g., reverse transcriptase or DNA polymerase.

An "isolated" nucleic acid or polypeptide as used herein refers to a component that is removed from its original environment (for example, its natural environment if it is naturally occurring or a reaction mixture if it is synthetic). An isolated nucleic acid or polypeptide typically contains less than about 50%, preferably less than about 75%, and most preferably less than about 90%, of the components with which it was originally associated.

A nucleic acid sequence that is "derived from" a designated sequence refers to a sequence that corresponds to a region of the designated sequence. This encompasses sequences that are homologous or complementary to the sequence.

An internal positive control (IPC) target nucleic acid refers to a synthetic nucleic acid sequence cloned into a plasmid vector which is subsequently linearized, typically by the action of a restriction endonuclease. An IPC will typically have multiple primer binding sequences surrounding a generic probe-binding region, and acts as a generic control against false negative results in nucleic acid amplification reactions.

The sequence of a preferred internal positive control target DNA is:

5'-CGCCAGCGTGGACCATCAAGTAGTAATGA ACGCACGGACGAGGACATCA TAGAGATTA-CACCTTTATCCACAGTTCTCG-GTCTAACGCAGCAGTCAGTG TATCAGCAC-CAGCATCCGTAGTGAGTCTTCAGTGTCTGCT CCAGGATCGT G-3'<SEQ ID NO 5>.

As used herein, conditions appropriate for reverse transcription, i.e., conditions in which an oligonucleotide will prime cDNA synthesis, encompass incubation of RNA and primer oligonucleotides with a reverse transcriptase enzyme and nucleotides at a temperature and for a time that results in synthesis of cDNA.

Nucleic acids comprising any of the sequences disclosed herein or subsequences thereof can be prepared by conventional methods. For example, DNA can be chemically synthesized using, e.g., the phosphoramidite solid support method of Matteucci et al., 1981, *J Am. Chem. Soc.* 103:3185, the method of Yoo el al., 1989, *J Biol Chem.* 764:17078, or other well known methods. The nucleic acids may also be modified by many means known in the art. Nonlimiting examples of such modifications include methylation, "caps", substitution of one or more of the naturally occurring nucleotides with an analog, and internucleotide modifications such as, for example, those with uncharged linkages (e.g., methyl phosphonates, phosphotriesters, phosphoroamidates, carbamates, etc.) or charged linkages (e.g., phosphorothioates, phosphorodithioates, etc.). Nucleic acids may contain one or more additional covalently linked moieties, such as, for example, proteins (e.g., nucleases, toxins, antibodies, signal peptides, poly-L-lysine, etc.), intercalators (e.g., acridine, psoralen, etc.), chelators (e.g., metals, radioactive metals, iron, oxidative metals, etc.), and alkylators. PNAs are also encompassed by the term "nucleic acid". The nucleic acid may be derivatized by formation of a methyl or ethyl phosphotriester or an alkyl phosphoramidate linkage. Furthermore, the nucleic acid sequences of the present invention may also be modified with a label capable of providing a detectable signal, either directly or indirectly. Exemplary labels include radioisotopes, fluorescent molecules, biotin, and the like.

Amplification as used herein refers to an iterative process by which a nucleic acid is copied. Suitable methods for amplification include without limitation the polymerase chain reaction, the ligase chain reaction, and transcription-mediated amplification.

Human Immunodeficiency Virus (HIV) as used herein refers to species in the genus of Retroviridae, including HIV-1, HIV-2, and SIV, and variant strains thereof. Isolates of HIV that may be detected by the present invention include, but are not limited to, HIV-1 and HIV-2.

The present invention provides methods for reverse transcribing HIV RNA from biological samples, which methods are useful for detection of HIV in biological samples. Detection of HIV-specific amplification products indicates the presence of HIV RNA in the sample.

According to the invention, a biological sample is obtained from a patient by any conventional means. Suitable biological samples include, without limitation, blood, serum, plasma, urine, breast milk, tissue samples, and cerebrospinal fluid. Preferably, plasma is used as the source of HIV RNA.

The biological sample is treated in any manner that provides access of the reverse transcription reagents to RNA, specifically HIV RNA, contained within the sample. RNA "derived from" a biological sample is any RNA which was originally present in the sample and to which access has been gained by treating the sample. Preferably, RNA is extracted from the sample using any method well known in the art, such as, e.g., methods employing guanidinium thiocyanate, or using commercially available reagents and methods such as, e.g., PureScript from Gentra Systems, Inc. (Minneapolis Minn.). Any extraction procedure may be used that results in separation from the RNA of RNases, other proteins, and/or any other components that might interfere with reverse transcription.

The RNA extracted from the sample is then contacted with oligonucleotide primers under conditions where the oligonucleotides prime the synthesis of DNA complementary to at least a portion of the extracted RNA. The sequences of the oligonucleotide primers are derived from the sequence of HIV. The primers correspond to regions of HIV RNA that may be downstream, i.e., 3', to regions whose detection is desired. These regions may include, e.g., the long terminal repeat (LTR) region, the region encoding the viral reverse transcriptase (Pol), Gag protein, Tat protein, envelope glycoprotein, Vif, Vpr, and Vpu proteins, and the Rev region, which encodes a transcription factor response element. Preferably, the primers correspond to sequences near the 3' end of the HIV genome. The primer sequences may be used to specifically identify particular isolates of HIV (e.g., isolates of HIV-1 and HIV-2). A primer may identify a particular isolate by hybridizing to RNA derived from that isolate under conditions in which it does not hybridize to RNA from a different isolate, i.e., the primer itself may comprise a sequence that differs between isolates. Alternatively, the primer sequence may be used to prime synthesis of a figment of HIV RNA that differs between isolates, i.e., the sequence that differs between the isolates may be downstream of the primer sequence.

Reverse transcription primers useful in practicing the present invention are selected based on theoretical considerations of sequence conservation, intra- and inter-molecular interactions, and the predicted secondary structures of the amplicon and surrounding sequence. Furthermore, the primers and assay system are designed to allow the co-amplification (and co-detection) of multiple regions of the HIV genome, multiple viral species, and an internal positive control (IPC) RNA (or DNA).

Non-limiting examples of reverse transcription primers according to the invention are shown in Table 1.

TABLE 1

| SOURCE | DESIGNA-TION | SEQUENCE | SEQ ID NO. |
| --- | --- | --- | --- |
| HIV-1 | POL3RT | 5'-CTTGTATTACTACTG-3' | 1 |
| HIV-1 | LTR8RT | 5'-CCCTGTGGCGCC-3' | 2 |
| HIV-2 | 2LTR1RT | 5'-GCGACTAGGAGAGA-3' | 3 |
| HIV-2 | 2Env2RT | 5'-CCCAGACGGTCAGT-3' | 4 |

Reverse transcription is performed using one or more of the above primers. Random primers, such as, e.g., random hexamer reverse transcription primers (N6, Pharmacia Biotech, Piscataway, N.J.) may also be added. Reverse transcription is carried out using conventional procedures, such as are described in *Current Protocols in Molecular Biology*, Volumes I, II, and III, 1997 (F. M. Ausubel ed.); in U.S. Pat. No. 5,322,770; in Young, et al., *J. Clin. Microbiol.* 31(4):882 (1993); Myers et al., *Biochemistry* 30(3):7661 (1991); or as described in copending U.S. provisional patent application Ser. No. 60/118,520 filed on Feb. 3, 1999.

Following the reverse transcription reaction, the cDNA product or products can be isolated and recovered by conventional methods. Preferably the cDNA product or products are amplified. Any method for amplification may be used, including, without limitation, polymerase chain reaction (PCR), ligase chain reaction, strand displacement amplification, transcript mediated amplification, and nucleic acid single base amplification. Preferably, PCR is used. Typically, a reaction mixture containing all of the necessary components for PCR (including HIV-specific amplification primers) is added directly to the reverse transcription reaction mixture. Amplification is then carried out using conditions specified by the primer pairs that are used. Suitable amplification primer pairs are disclosed, e.g. in U.S. provisional patent application Ser. No. 60/118,498 filed on Feb. 3, 1999.

Following amplification, the amplification products may be detected using any method known in the art, including, without limitation, gel electrophoresis in agarose or acrylamide; capture of the amplification products on a solid support followed by colorimetric detection (see, e.g., Example 1 below); ECi detection; fluorescence, radioisotopic detection, and chemiluminescence. Reagents for such detection methods are commercially available from., e.g, Molecular Probes, Eugene, Oreg. and Ortho Clinical Diagnostics, Rochester, N.Y.

The detection of HIV-specific amplification products indicates the presence of HIV RNA in the sample. When gel electrophoresis is used, HIV-specific amplification products are confirmed by their size, as predicted by the location in HIV RNA of the sequences corresponding to the amplification primers used in the reaction.

The present invention provides kits for detection of HIV RNA in biological samples, which comprise one or more of the reverse transcription primers shown in Table 1 above. The kits may also comprise reagents for reverse transcription, as well as additional reagents for detection of HIV cDNA by, e.g., PCR.

DESCRIPTION OF THE PREFERRED EMBODIMENTS

The following examples illustrate the present invention without limitation.

Methods:

1. Sample preparation:

RNA was prepared from plasma samples using guanidinium thiocyanate or PureScript® RNA isolation reagents (Gentra Systems, Minneapolis Minn.). Modifications to the manufacturer's protocol for body fluids included use of 40 μkg glycogen, rather than 20 μg, as a carrier to aid in the precipitation of viral RNA. Additionally, in most cases, after isopropyl alcohol precipitation of the RNA and washing the RNA pellet with ethanol, the RNA pellet was resuspended in the RT buffer mix, rather than in the RNA hydration solution provided by the manufacturer.

2. Reverse Transcription:

The synthesis of cDNA from RNA was catalyzed by the addition of 100 U recombinant Moloney Murine Leukemia Virus (M-MLV) reverse transcriptase (RT) (Gibco BRL, Gaithersburg, Md.) in a 50 μl solution of 50 mM Tris-HCl (pH 8.3), 75 mM KCl, 3 mM $MgCl_2$, 10 mM DTT, 0.4 mM of each dNTP (Pharmacia Biotech), 4 μM random hexamers Pharmacia Biotech, Piscataway, N.J.) and/or specific reverse transcription primer, and 20 units RNasin (Promega, Madison, Wis.) in diethylpyrocarbonate (DEPC)-treated water. After incubation at 42° C. for 30 min, the RT reaction was held at 100° C. for 5 min to destroy RT activity. Each reaction was chilled for 1 min followed by microcentrifugation at 16000×g for 4 seconds.

3. PCR Amplification:

PCR was carried out IN A PE9600 thermocycler (Perkin-Elmer) in a 100 μl solution of 25 mM Tris-HCl, 3 mM $MgCl_2$, 0.725 mM EDTA, 54 mM KCl, 3.72 mM NaCl, 40 μM DTT, 108 μg/mL gelatin (type IV), 9.5% glycerol, 0.02% Tween 20, 0.02% NP40, calf thymus DNA (2 μg), 1.2 mM of each dNTP, 0.4 μM of each primer, 10 copies linearized internal positive control (IPC) plasmid DNA, and 16 U of Taq polymerase. Monoclonal antibodies to Taq, TP1-12 and TP4-9, the preparation of which are disclosed in U.S. Pat. No. 5,338,671, were added to the reaction at a 50:1 and 5:1 molar ratio, respectively, to provide a 55:1 molar ratio of antibody to Taq polymerase. After initial denatur ation at 96° C. for 3 min, 40 cycles of amplification were performed at 96° C. for 5 sec and 68° C. for 40 sec. At the conclusion of cycling, a post-heat step was performed for 5 min at 103° C. to inactivate Taq polymerase. The amplification primers used are shown in Table 2 below.

TABLE 2

| ID | Source | Sequence | SEQ ID NO. |
|---|---|---|---|
| JBLT R4 | HIV-1(s) | 5'-CTG CTT AAG CCT CAA TAA AGC TTG CCT TGA-3' | 6 |
| JBLT R6 | HIV-1(as) | 5'-GGG TCT GAG GGA TCT CTA GTT ACC AGA GT-3' | 7 |
| JBLT R8 | HIV-1(as) | 5'-TGT TCG GGC GCC ACT GCT AGA GA-3' | 8 |
| 2LTRe | HIV-2(s) | 5'-GGG AGG TTC TCT CCA GCA CTA GCA-3' | 9 |
| 2LTR-R1 | HIV-2 (as) | 5'-GCG ACT AGG AGA GAT GGG AAC ACA CA-3' | 10 |

4. Detection of PCR Products:

PCR products were detected either by (i) gel electrophoresis, followed by ethidium bromide staining; or (ii) use of 5'-biotin-labeled primers (sense strand) during amplification. In this case, the amplification products were captured by hybridization to oligonucleotide probes covalently attached to latex particles, which were deposited on the surface of a flow through membrane (SureCell® tests, Ortho Clinical Diagnostics, Rochester, N.Y.). The HIV-1 probes were: 5'-CAACAGACGGGCACACACTACT-3' (JBLTRpr) <SEQ ID NO 11> and 5'-GAACAGATGGGCACACACTGCT-3'(JBLTRpr4) <SEQ ID NO 12>; and the HIV-2 probe was 5'-CCACGCTTGCTTGCTTAAAGACCTC-3'(2LTRpr1) <SEQ ID NO 13>. The probe/product complex was reacted with streptavidin (SA)-horseradish peroxidase (BRP) conjugate, which catalyzes the oxidative conversion of a dye precursor to a dye (blue color). The blue color intensity was scored visually (0-10) by comparing color intensity to color standards. All visual color scores >3 were considered to be positive results.

EXAMPLE 1

Efficiency of Reverse Transcription Using HIV-Specific Primers or Random Primers The following experiment was performed to compare the efficiency of reverse transcription of HIV RNA derived from human plasma samples using HIV-specific primers according to the invention or random hexamer reverse transcription primers (N6, Pharmacia Biotech).

Human plasma was diluted to contain 1000 copies of HIV RNA per 100 µl, to yield approximately 100 copies of HIV RNA per reaction. RNA was extracted from the plasma using guanidinium thiocyanate. The RNA pellet was dissolved in 26 µl of diethylpyrocarbonate-treated water.

The reverse transcription reaction contained: 13 µl RNA, 10 µl reverse transcription mix (which contained first-strand buffer, 0.1 M DTT, 20 U RNasin (Promega, Madison, Wis.), 0.4 mM of each dNTP, and 200 Units of Moloney Murine Leukemia Virus (M-MLV) reverse transcriptase). An additional 2 µl of the following primer mixes (all at 50 µM) were added according to the condition being tested: (1) 2 µl N6 random primers; (2) 1 µl N6 random primers+1 µl LTR8RT primer; (3) 1 µl N6 random primers+1 µl POL3RT primer; (4) 1 µl LTR8RT+1 µl POL3RT. The reverse transcription reaction was incubated at 42° C. for 30 minutes; heated to 100° C. for 5 minutes; and then chilled on ice for 1 minute. A 75 µl PCR master mix was then added to the cDNA-containing reaction mixture and PCR was performed under the following conditions: a 3 minute preheat at 96° C., followed by 5 cycles of melting at 96° C. followed by annealing and amplification at 62° C. for 5 seconds, followed by 35 cycles of melting at 96° C. and annealing and amplifying at 68° C. for 40 seconds. The amplification products were then resolved in a 4% agarose gel and visualized using ethidium bromide.

Figure 2:
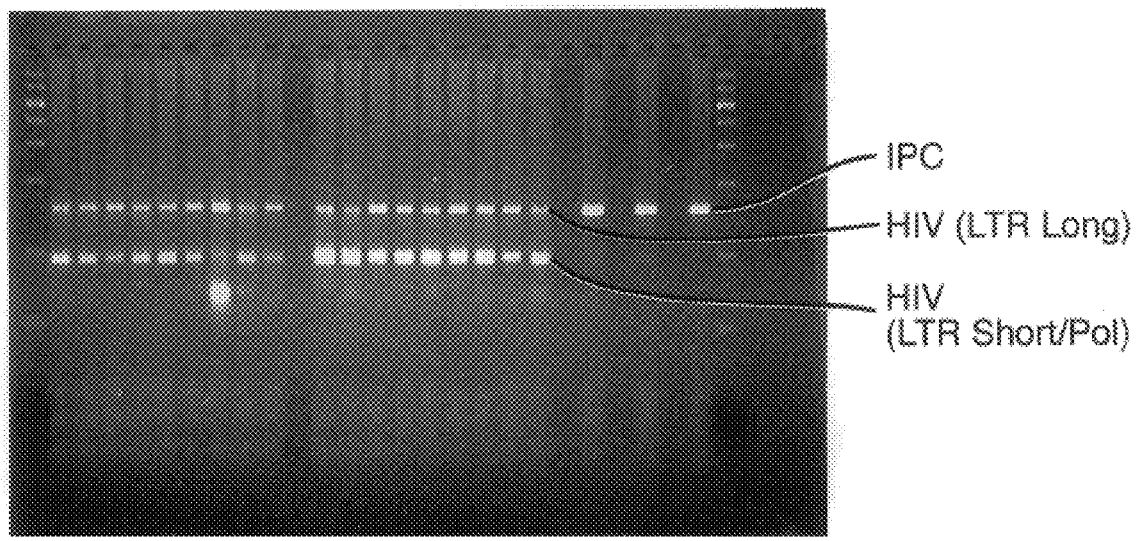
FIG. 2 is a photographic illustration of a 4% agarose gel stained with ethidium bromide showing HIV-1-specific amplification products obtained using as a reverse transcription primer (a) a mixture of random hexamer primers and POL3RT (lanes 2–10) or (b) a mixture of LTR8RT and POL3RT (lanes 12–20). Lane 1 contains markers, and lanes 22, 24, and 26 are control samples.

Results: As illustrated in FIGS. 1 and 2, the use of HIV-specific reverse transcription primers, either alone or in conjunction with random hexamer primers, results in the detection of significantly more HIV-1-specific amplification products. Compare FIG. 1, lanes 2–10 (random primer alone) with FIG. 1, lanes 12–20 (LTR8RT+random primer); FIG. 2, lanes 2–10 (POL3RT+random primer); and FIG. 2, lanes 12–20 (LTR8RT+POL3RT). This result was also observed in when 100 µM or 200 µM random primers were used.

EXAMPLE 2

Detection of HIV RNA in Patient Samples

The following study was performed to compare the detection of HIV RNA in patient samples using either random hexamer reverse transcription primers or random primers in conjunction with HIV-specific reverse transcription primers.

HIV-positive plasma samples were collected from patients having CD4 T-cell counts greater than 500, indicating that they were asymptomatic and had a relatively low viral load.

RNA was extracted from the plasma samples as described in Example 1 above. 13 µl of the RNA solution were diluted in 15 µl water. Each sample was split into two 12-µl aliquots for reverse transcription. Two reverse transcription reaction mixes were prepared with as described in Example 1 above. Each mix contained either 2 µl of 100 µM random primer+1 µl water or 2 µl of 100 µM random primer+1 µl of a 50 µM HIV-specific primer mix containing equal amounts of the following primers: (1) POL3RT; (2) LTR8RT; (3) 2LTRRT; and (4) 2EnvRT. The reverse transcription and amplification reactions were performed as described in Example 1 above.

HIV-specific amplification products were detected by gel electrophoresis on 4% agarose gels stained with Ethidium Bromide and also by the SureCell® colorimetric method described above.

Figure 3:
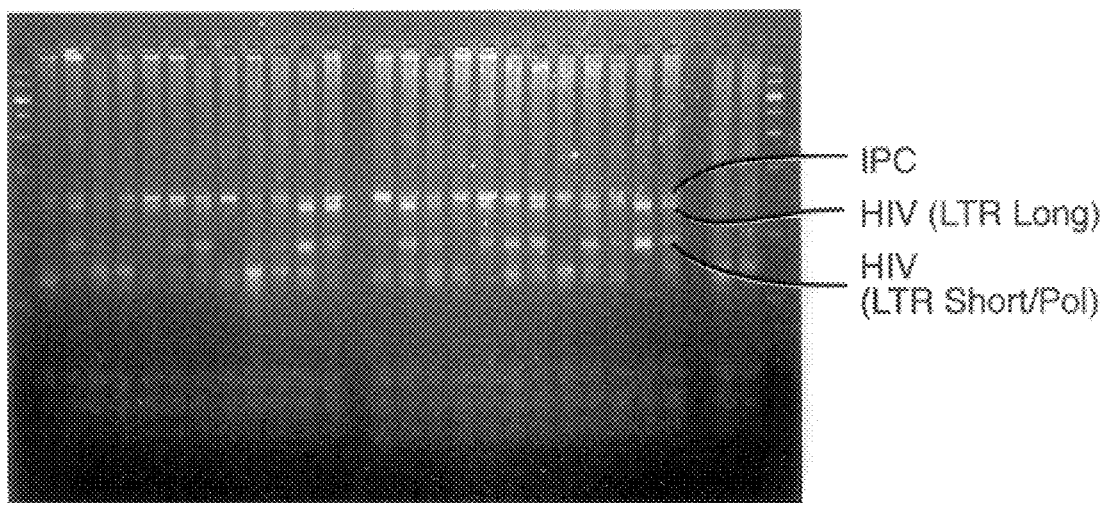
FIG. 3 is a photographic illustration of a 4% agarose gel stained with ethidium bromide showing HIV-1-specific amplification products obtained using (a) random hexamer primers (lanes 2–13) or (b) random hexamer and a mixture of POL3RT, LTR8RT, 2LTRRT and 2EnvRT (lanes 15–26). Lane 1 contains markers.
Figure 4:
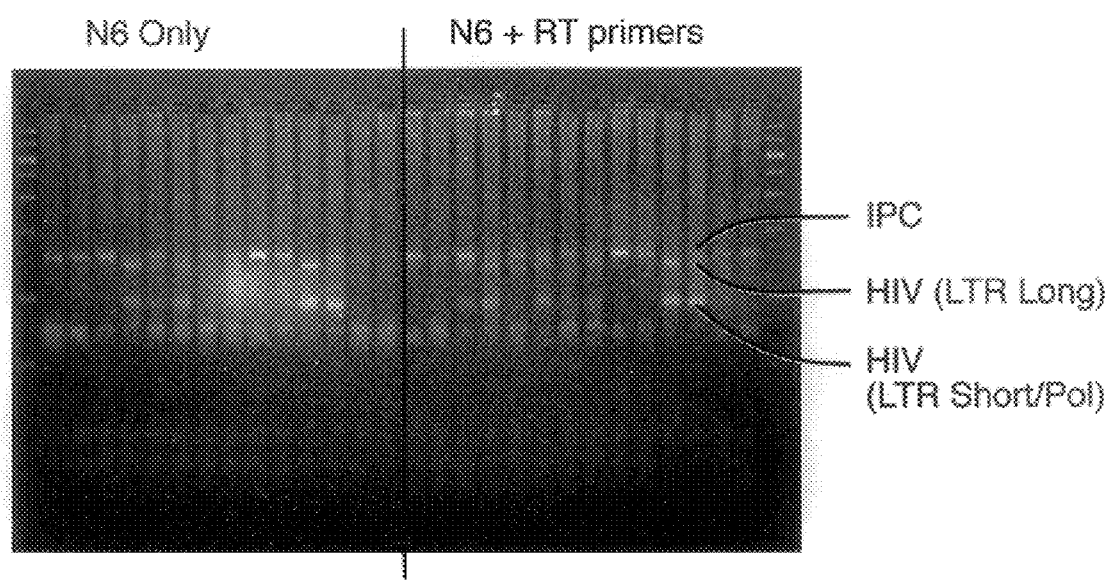
FIG. 4 is a photographic illustration of a 4% agarose gel stained with ethidium bromide showing HRV-1-specific amplification products obtained using (a) random hexamer primers (lanes 2–15) or (b) random hexamer and a mixture of POL3RT, LTR8RT, 2LTRRT and 2EnvRT (lanes 16–29). Lanes 1 and 30 contain markers.

Results: FIGS. 3 and 4 illustrate the amplification products detected by gel electrophoresis. Detection of HIV-specific amplification products by the colorimetric method is indicated in relative values in Table 3. IPC indicated internal positive control primers.

TABLE 3

| | RANDOM PRIMERS ONLY | | | N6 + RT PRIMERS | | |
|---|---|---|---|---|---|---|
| Sample | LTR 3/4 | POL 3/4 | IPC 1P | LTR 3/4 | POL 3/4 | IPC 1P |
| 1 | 0 | 0 | 8 | 0 | 0 | 8 |
| 2 | 8 | 7 | 8 | 8 | 7 | 7.5 |

TABLE 3-continued

| Sample | RANDOM PRIMERS ONLY | | | N6 + RT PRIMERS | | |
|---|---|---|---|---|---|---|
| | LTR 3/4 | POL 3/4 | IPC 1P | LTR 3/4 | POL 3/4 | IPC 1P |
| 3 | 5 | 6 | 8 | 7 | 7 | 7.5 |
| 4 | 5 | 5 | 8 | 5 | 5 | 8 |
| 5 | 7 | 5 | 8 | 7.5 | 7.5 | 8 |
| 6 | na | na | na | na | na | na |
| 7 | 6 | 7 | 8 | 5 | 7.5 | 8 |
| 8 | 8 | 8 | 8 | 8 | 8 | 8 |
| 9 | 2 | 2 | 8 | 3 | 0 | 8 |
| 10 | 5 | 7 | 8 | 7 | 8 | 8 |
| 11 | 6 | 7 | 8 | 6 | 6 | 8 |
| 12 | 8 | 8.5 | 8 | 7.5 | 9 | 7.5 |
| 13 | 8 | 7.5 | 8 | 8 | 7.5 | 8 |
| 14 | 0 | 0 | 8 | 0 | 0 | 9 |
| 15 | 0 | 0 | 8 | 0 | 0 | 8 |
| 16 | 2 | 0 | 8 | 7 | 8 | 9 |
| 17 | 7.5 | 7.5 | 8 | 7.5 | 7.5 | 8 |
| 18 | 6 | 7 | 8 | 6 | 7 | 8 |
| 19 | 7.5 | 7.5 | 7.5 | 7.5 | 8 | 8 |
| 20 | 2 | 1 | 8 | 5 | 5 | 8 |
| 21 | 6.5 | 6.5 | 8 | 7 | 7.5 | 7 |
| 22 | 1 | 1 | 8 | 3 | 5 | 8 |
| 23 | 3 | 1 | 8 | 2 | 2 | 8 |
| 24 | 7 | 9 | 8 | 7 | 9 | 7 |
| 25 | na | na | na | na | na | na |
| 26 | 9 | 9 | 7 | 9 | 9 | 6.5 |
| 27 | 3 | 4 | 7 | 5 | 7 | 8.5 |
| 28 | 2 | 2 | 8 | 2 | 2 | 8.5 |
| Neg | 0 | 0 | 7 | 0 | 0 | 7 |
| Pos | 5 | 5 | 7 | 5 | 5 | 7 |

In samples 3 and 10, the addition of HIV-specific RT primers to the random hexamer primers resulted in a greater degree of amplification than using random primers alone. The amount of product detected by the calorimetric method was also greater in these samples when HIV-specific RT primers were used.

Samples 16, 20, and 22 were not detected using only random primers in the reverse transcription reaction, either by gel electrophoresis or by colorimetry. These samples, however, were positive when HIV-specific RT primers were used in addition to random primers.

These results indicate that the methods and compositions of the present invention can reduce the incidence of false negative results in screening of patients or blood supply for HIV.

All patents, applications, articles, publications, and test methods mentioned above are hereby incorporated by reference in their entirety.

Many variations of the present invention will suggest themselves to those skilled in the art in light of the above detailed description. Such obvious variations are within the full intended scope of the appended claims.

What is claimed is:

1. A method for reverse transcribing Human Immunodeficiency Virus (HIV) RNA in a biological sample, said method comprising:

(a) contacting RNA derived from said sample with an oligonucleotide under conditions in which said oligonucleotide primes synthesis of DNA complementary to at least a portion of said RNA; wherein said oligonucleotide is selected from the group consisting of:
   (i) 5'-CTTGTATTACTACTG-3'<SEQ ID NO 1>,
   (ii) 5'-CCCTGTGGCGCC-3'<SEQ ID NO 2>,
   (iii) 5'-GCGACTAGGAGAGA-3'<SEQ ID NO 3>,
   (iv) 5'-CCCAGACGGTCAGT-3'<SEQ ID NO 4>, and
   (v) any two or more of the foregoing.

2. A method as defined in claim 1, wherein said sample is selected from the group consisting of blood, serum, plasma, urine, saliva, and cerebrospinal fluid.

3. A method as defined in claim 1, further comprising (b) recovering said cDNA.

4. A method for detecting the presence of Human Immunodeficiency Virus (HIV) RNA in a biological sample, said method comprising:

(a) performing a reverse transcription reaction, using RNA derived from said sample as a template and using an oligonucleotide complementary to a nucleotide sequence contained within said RNA as a reverse transcription primer to produce HIV-specific reverse transcription products, wherein said reverse transcription primer is selected from the group consisting of:

(i) 5'-CTTGTATTACTACTG-3'<SEQ ID NO 1>,
(ii) 5'-CCCTGTGGCGCC-3'<SEQ ID NO 2>,
(iii) 5'-GCGACTAGGAGAGA-3'<SEQ ID NO 3>,
(iv) 5'-CCCAGACGGTCAGT-3'<SEQ ID NO 4>, and
(v) any two or more of the foregoing;

(b) amplifying said reverse transcription products to produce amplification products; and (c) detecting said amplification products;

wherein detection of said amplification products of said amplification indicates the presence of HIV RNA in said sample.

5. A method as defined in claim 4, wherein said sample is selected from the group consisting of blood, serum, plasma, urine, saliva, and cerebrospinal fluid.

6. A method as defined in claim 4, wherein said amplifying is performed by a method selected from the group consisting of polymerase chain reaction, ligase chain reaction, and strand displacement amplification.

7. A method as defined in claim 4, wherein said detecting is performed by a method selected from the group consisting of gel electrophoresis of amplification products, capture of amplification products on solid supports, and chemiluminescent detection of amplification products.

8. The oligonucleotide 5'-CTTGTATTACTACTG-3'<SEQ ID NO 1>.

9. The oligonucleotide 5'-CCCTGTGGCGCC-3'<SEQ ID NO 2>.

10. The oligonucleotide 5'-GCGACTAGGAGAGA-3'<SEQ ID NO 3>.

11. The oligonucleotide 5'-CCCAGACGGTCAGT-3'<SEQ ID NO 4>.

12. An HIV-specific reverse transcription primer comprising the oligonucleotide 5'-CTTGTATTACTACTG-3'<SEQ ID NO 1>.

13. An HIV-specific reverse transcription primer comprising the oligonucleotide 5'-CCCTGTGGCGCC-3'<SEQ ID NO 2>.

14. An HIV-specific reverse transcription primer comprising the oligonucleotide 5'-GCGACTAGGAGAGA-3'<SEQ ID NO 3>.

15. An HIV-specific reverse transcription primer comprising the oligonucleotide 5'-CCCAGACGGTCAGT-3'<SEQ ID NO 4>.

16. A kit for detection of HIV-1, HIV-2, or a combination thereof, in a biological sample, said kit comprising a reverse transcription primer selected from the group consisting of:

(a) 5'-CTTGTATTACTACTG-3'<SEQ ID NO 1>,
(b) 5'-CCCTGTGGCGCC-3'<SEQ ID NO 2>,
(c) 5'-GCGACTAGGAGAGA-3'<SEQ ID NO 3>,
(d) 5'-CCCAGACGGTCAGT-3'<SEQ ID NO 4>,
(e) any two or more of the foregoing.

17. A method as defined in claim 1, further comprising simultaneously contacting RNA derived from said sample with random hexamer oligonucleotides under conditions in which said random hexamer oligonucleotides prime synthesis of DNA complementary to at least a portion of said RNA.

18. A method as defined in claim 4, wherein in step (a) random hexamer oligonucleotides are also used as reverse transcription primers.

* * * * *